United States Patent

Askew et al.

[11] 4,141,851
[45] Feb. 27, 1979

[54] SILANE DERIVATIVES

[75] Inventors: Herbert F. Askew, Wokingham; Colin J. Harrington, Reading; Gerald J. J. Jayne, Wokingham, all of England

[73] Assignee: Castrol Limited, Wiltshire, United Kingdom

[21] Appl. No.: 868,912

[22] Filed: Jan. 12, 1978

Related U.S. Application Data

[63] Continuation of Ser. No. 742,995, Nov. 18, 1976, abandoned.

[30] Foreign Application Priority Data

Nov. 21, 1975 [GB] United Kingdom ............... 48009/75

[51] Int. Cl.² ............................ C09K 3/00; C07F 7/18
[52] U.S. Cl. ............................ 252/78.3; 260/448.8 R
[58] Field of Search ................. 260/448.8 R; 252/78.3

[56] References Cited

U.S. PATENT DOCUMENTS

| | | | |
|---|---|---|---|
| 2,846,458 | 8/1958 | Haluska | 260/448.8 R X |
| 3,308,149 | 3/1967 | Schenck et al. | 260/448.8 R |
| 3,383,315 | 5/1968 | Gothel et al. | 260/448.8 R X |
| 3,509,192 | 4/1970 | Niederprum et al. | 260/448.8 R |
| 3,803,197 | 4/1974 | Anderson et al. | 260/448.8 R X |
| 3,814,691 | 6/1974 | Csejka et al. | 252/78.3 |
| 3,994,948 | 11/1976 | Jayne et al. | 260/448.8 R |
| 4,051,053 | 9/1977 | Elliott et al. | 252/78.3 |

FOREIGN PATENT DOCUMENTS 1359956 7/1974 United Kingdom ...... 260/448.8 R UX

OTHER PUBLICATIONS

"Chemical Abstracts", 76, p. 99754c, 1972.

Primary Examiner—Paul F. Shaver
Attorney, Agent, or Firm—Bacon & Thomas

[57] ABSTRACT

Novel silane derivatives having the general formula:

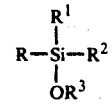

wherein:
(a) R is a group of the formula $R^4-(OR^5)_m-OR^6-$;
(b) each of $R^1$ and $R^2$ is independently alkyl, alkenyl, aryl, alkaryl or aralkyl, a group of the formula $-OR^3$ or a group of the formula $R^4-(OR^5)_m-OR^6-$;
(c) $R^3$ is a group of the formula $R^4-(OR^5)_m-$ or a group of the formula:

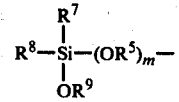

(d) $R^4$ is alkyl, alkenyl, aryl, alkaryl or aralkyl;
(e) $R^5$ is alkylene;
(f) $R^6$ is alkylene;
(g) m is zero or an integer;
(h) each of $R^7$ and $R^8$ is independently alkyl, alkenyl, aryl, alkaryl or aralkyl, a group of the formula $-OR^9$ or a group of the formula $R^4-(OR^5)_m-OR^6-$; and
(i) $R^9$ is a group of the formula $R^4-(OR^5)_m-$.

Also disclosed are hydraulic fluids containing the novel compounds.

23 Claims, No Drawings

SILANE DERIVATIVES

This is a continuation, of application Ser. No. 742,995, filed Nov. 18, 1976 now abandoned.

This invention relates to certain novel silane derivatives which are useful as components of hydraulic fluids and to hydraulic fluids containing such compounds.

Hydraulic fluids based on glycol ethers have been used in, for example, vehicle brake and clutch systems for many years and still remain the most commonly used type of fluid. However, specifications of required quality standards laid down by hydraulic systems manufacturers and non-commercial organisations such as the Society of Automotive Engineers and the U.S. Department of Transportation have become progressively more severe. In particular, a need has arisen for fluids having higher boiling points and, more importantly, higher vapour lock temperatures both for the fluid as formulated by the manufacturers and also for the fluid in the presence of water. Glycol ether based fluids are known to be deficient in this respect due to the hygroscopicity of the fluid which results in the absorption of water from the atmosphere. This in turn reduces the boiling point and vapour lock temperature of the fluid and with extended use the water content of the fluid can build up to a level at which the boiling point and vapour lock temperatures are reduced to a dangerous extent. When subjected to heat, e.g. generated by heavy braking, the fluid may boil or vaporise to a sufficient extent to cause a serious brake malfunction.

Hydraulic fluids having low hygroscopicity have been developed, based on glycol esters, to deal with this problem. Such fluids are relatively insensitive to the effect of atmospheric moisture, but are more expensive than glycol ether based fluids and have certain technical disadvantages, e.g. their viscosity properties are inferior to those of glycol ether based fluids. Consequently, use of these low hygroscopicity fluids has been mainly limited to where the desirable properties such as high boiling point and vapour lock temperatures are deemed to outweigh their disadvantages. Other types of water insensitive fluids have also been developed. Nevertheless, manufacturers are still seeking new fluids which combine as many as possible of the desirable properties of both glycol ether based and low hygroscopicity fluids and, desirably, have even higher boiling points and/or vapour lock temperatures than the low hygroscopicity fluids.

Recently, there has emerged a growing tendency in vehicle design to use a single hydraulic system to operate equipment, such as power-steering, shock absorbers and brakes, which hitherto were provided with separate hydraulic systems. This has created serious problems in the formulation of suitable fluids. The mineral oil based fluids hitherto used in power-steering systems and shock absorbers are satisfactory with respect to the nitrile and chloroprene rubber used for the seals and gaskets in such systems but are highly detrimental to the natural and styrene/butadiene rubbers used in the construction of hydraulic brake and clutch systems. This results in excessive swelling of the latter seals which can lead to a serious malfunction of the brake or clutch system. Conversely, the fluids hitherto used in brake and clutch systems, which are normally based on glycols, glycol ethers and/or glycol ether esters, and which have operated satisfactorily in such systems, have a detrimental effect on the nitrile and chloroprene rubber gaskets used in power-steering systems and shock absorbers which can also lead to malfunctioning. In the case of vehicle operation the characteristic of reliability in operation, which is generally desirable in all mechanical devices, is increased in importance to an absolutely essential requirement by virtue of safety considerations. The need has therefore arisen for a fluid which can be used satisfactorily in a central system controlling the operation of a number of different items of equipment.

We have now found certain novel silicon compounds which are useful as components of hydraulic fluids, for hydraulic brake and clutch systems and also for central hydraulic systems. These compounds exhibit improved rubber swell properties with respect to a variety of natural and synthetic rubbers used in the construction of hydraulic systems and they are also relatively water insensitive.

Accordingly, the present invention provides, as novel compounds, silane derivatives having the general formula:

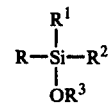

wherein:
(a) R is a group of the formula $R^4-(OR^5)_m-OR^6-$;
(b) each of $R^1$ and $R^2$ is independently alkyl, preferably containing from 1 to 18 carbon atoms, more preferably methyl; alkenyl, preferably containing from 1 to 18 carbon atoms; aryl, preferably phenyl; alkaryl, preferably alkyl substituted phenyl in which the alkyl substituent contains from 1 to 12 carbon atoms; or aralkyl, preferably benzyl; a group of the formula $-OR^3$; or a group of the formula $R^4-(OR^5)_m-OR^6-$;
(c) $R^3$ is a group of the formula $R^4-(OR^5)_m-$ or a group of the formula:

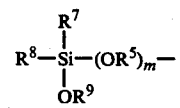

and each $R^3$ may be the same as or different from any other group $R^3$;
(d) $R^4$ is alkyl, preferably containing from 1 to 18 atoms; alkenyl, preferably containing from 1 to 18 carbon atoms; aryl preferably phenyl; alkaryl, preferably alkyl substituted phenyl in which the alkyl substituent contains from 1 to 12 carbon atoms; or aralkyl, preferably benzyl; and each $R^4$ may be the same as or different from any other group $R^4$;
(e) $R^5$ is an alkylene group, preferably containing from 1 to 15, more preferably 1 to 4 carbon atoms, especially ethylene or propylene; and each $R^5$ may be the same as or different from any other group $R^6$;
(f) $R^6$ is an alkylene group, preferably containing from 1 to 15, more preferably 1 to 6, carbon atoms; and each $R^6$ may be the same as or different from any other group $R^6$;
(g) m is zero or an integer, preferably zero or an integer of from 1 to 4; and each m may be the same as or different from any other m;

(h) each of $R^7$ and $R^8$ is independently alkyl, preferably containing from 1 to 18 carbon atoms, more preferably methyl; alkenyl, preferably containing from 1 to 18 carbon atoms; aryl, preferably phenyl; alkaryl, preferably alkyl substituted phenyl in which the alkyl substituent contains from 1 to 12 carbon atoms; or aralkyl, preferably benzyl; a group of the formula $-OR^9$; or a group of the formula $R^4-(OR^5)_m-OR^6-$; and (i) $R^9$ is a group of the formula $R^4-(OR^5)_m-$ and each $R^9$ may be the same as or different from any other group $R^9$.

It is preferred that the silane derivatives of the invention contain no more than 2 silicon atoms.

In another aspect of the present invention there is provided a hydraulic fluid containing one or more silane derivatives as defined above.

In the case of silane derivatives for use in hydraulic brake and clutch systems it is preferable for any terminal alkyl groups present to be relatively short chain alkyl groups, e.g. containing from 1 to 4, more preferably 1 or 2, carbon atoms, in order to minimise the rubber swelling effect on the seals and gaskets used in such systems. However when used in a central system it may be more desirable to effect a compromise between the requirements, often conflicting, for each of the various seal and gasket materials. In this case some, or all, of the terminal alkyl groups may be longer chain alkyl groups, e.g. up to 6, or even 8, carbon atoms. Furthermore, in the case of fluids based on mineral oil, even longer chain terminal alkyl groups, e.g. containing up to 16, or even 18, carbon atoms, may be necessary in order to effect oil solubility. The terminal alkyl groups may be straight or branched chain but for oil solubility, particularly in mineral oil, branched chain alkyl groups are preferred.

The silane derivatives of the present invention may be readily prepared from appropriate haloalkyl silanes using well-known techniques.

The silane derivatives of the invention may be used in hydraulic fluids as an additive, as a base stock or as a component of a blend of base stocks. The proportions employed may therefore vary over a very wide range e.g. from 0.5 to 99% by weight based on the total weight of the hydraulic fluid. When used as a base stock the silane derivatives will constitute the bulk of the hydraulic fluid, for example from 75% or 80% to 99% by weight, based on the total weight of the hydraulic fluid. The remainder of the hydraulic fluid may be composed of conventional hydraulic fluid additives and/or small quantities of other hydraulic fluid base-stocks.

When used as a component of a blend of base stocks the total blend of base stocks will likewise constitute the bulk of the hydraulic fluid. In this case, the base stocks may be predominantly one or more silane derivatives blended with a lesser quantity of one or more other base stocks so as to modify the properties of the silane derivatives. Thus, the hydraulic fluid may contain, for example 55% to 75% by weight of one or more silane derivatives based on the total weight of the hydraulic fluid. Alternatively, one or more other base stocks may be modified by blending with a lesser quantity of silane derivatives so that the hydraulic fluid contains, e.g. from 20% to 40% by weight silane derivative. In addition, a compromise between the properties of the silane derivatives and the other fluids may be effected by blending in approximately equal quantities to provide fluids containing from 40% to 55% silane derivative.

When used to suppress the sensitivity of hydraulic fluids, and in particular the boiling point and vapour lock temperatures of the fluids, to water the silane derivatives are preferably used in amounts in the range of 20% to 55%, more preferably 20% to 40%. Alternatively but less preferably, an improvement can also be obtained using lower amounts of the silane derivatives, e.g. from 0.5% to 15% or 20% by weight based on the total weight of the hydraulic fluids. The bulk of such fluids will be constituted by one or more base stocks such as hereinafter described.

When the silane derivatives are used as a component of a blend of base stocks the resulting hydraulic fluids may contain conventional hydraulic fluid additives in like manner as when the base stock substantially consists of the silane derivatives. Similarly, when used as an additive the silane derivatives may, if desired, be used in conjunction with conventional hydraulic fluid additives.

Conventional additives are normally employed in small amounts such as 0.05% to 10%, for example, 0.1 to 2% by weight.

Base stocks with which the silane derivatives may be blended, or with which they may be used as additives, include mineral oil, polyoxyalkylene glycols and ethers thereof, alkyl and polyoxyalkylene glycol ether esters of mono-, di or poly carboxylic acids or boric acid, formals, acetals, phosphate esters, silicones, monocarboxylic acid esters of di- or polyalcohols and similar fluids well known in the art.

In a particular aspect of the invention there is provided a hydraulic fluid consisting essentially of a combination of from 5 to 30% by weight of at least one silane derivative of Formula I as hereinbefore defined and from 5 to 30% by weight of at least one compound having the general formula:

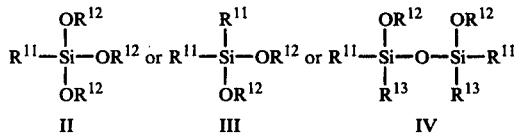

wherein $R^{11}$ is alkyl, preferably containing from 1 to 18 carbon atoms, or aryl, preferably phenyl; $R^{12}$ is alkyl, preferably containing from 1 to 18 carbon atoms, aryl, preferably phenyl, alkaryl, preferably alkyl substituted phenyl in which the alkyl substituent contains from 1 to 12 carbon atoms, or aralkyl, preferably benzyl, or a group of the formula $R^4-(OR^5)_m-$; $R^{13}$ is alkyl, preferably containing from 1 to 18 carbon atoms, aryl, preferably phenyl, alkaryl, preferably alkyl substituted phenyl in which the alkyl substituent contains from 1 to 12 carbon atoms, or aralkyl, preferably benzyl, or a group of the formula $R^4-(OR^5)_m-O-$; and $R^4$, $R^5$ and m are as hereinbefore defined, in a glycol ether base stock.

In a further particular aspect of the invention there is provided a hydraulic fluid consisting essentially of from 10 to 90% by weight of at least one silane derivative of Formula I as hereinbefore defined and from 90 to 10% by weight of at least one compound of Formula II, III or IV as hereinbefore defined.

Regardless of precise composition it is highly desirable that the hydraulic fluids of the present invention have a kinematic viscosity at $-40°$ C. of not more than 5,000 cSt, especially not more than 2,000 cSt. It is also desirable that the hydraulic fluids have a boiling point of at least 260° C.

In a further aspect of the present invention there is provided a hydraulic system for transmitting power by hydraulic means which system contains as the functional fluid, a hydraulic fluid as hereinbefore described.

In yet another aspect of the present invention there is provided a method of operating a hydraulic system which comprises introducing into the hydraulic system a hydraulic fluid as hereinbefore described and transmitting power by applying pressure to the hydraulic fluid.

The present invention will now be illustrated with reference to the following Examples:

EXAMPLE 1

Tris(methoxy)-3-chloropropyl silane (794 g; 4 moles) and methyl triglycol (2296 g; 14 moles) were heated under nitrogen cover in a glass flask fitted with a 1 ft packed column until 188.1 g of MeOH had been removed from the mixture. The column was removed and heating continued at a bottom temperature of 200° C. until 317.4 g (calc. 384) had been obtained.

Sodium (101.2 g; 4.4 g atom) was dissolved in methyl triglycol (1000 g, 6.1 mole) and the resultant slurry added to the reaction mixture which was maintained at 100° C. for 3 hours. The product was filtered, stripped under 0.1 mm Hg at a bottom temperature of 180° C., and refiltered.

2660 g (92%) of a dark liquid was obtained containing 4.20% Si, (calc. 3.88% Si for tris (methyltriglycol)-3-methyltriglycolpropyl silane). The product had a boiling point of 320° C. and a viscosity at $-40°$ C. of 2306 cS. Good results were obtained with rubber swell tests on SBR G9 (4.2%) and Natural R32 ($-1.0\%$).

EXAMPLE 2

Tris (methyldiglycol)-3-methyldiglycolpropyl silane was prepared in similar manner from tris(methoxy)-3-chloropropyl silane (198.5 g; 1 mole), methyl diglycol (396 g; 3.3 mole) and sodium (25 g; 1.1 g atom) in methyl diglycol (400 g; 3.4 mole).

77 g (calc. 96 g) of MeOH was collected in the first stage. 409 g (75%) of product was obtained containing 6.092% Si (calc. 5.12) and 0.2% chlorine. The product had a viscosity at $-40°$ C. of 1051 cS, a boiling point of 310° C. and gave good results in rubber swell tests: SBR G9 8.9% and Natural R32 2.0%.

EXAMPLE 3

Tris (tridecanoxy)-4-tridecanoxypropyl silane was prepared in similar manner from 3-chloropropyl-trimethoxy silane (397 g; 2 mole) and tridecanol (1400 g; 7 mole) and p-toluene sulphonic acid (0.2 g) and sodium (50.6 g; 2.2 g atom) in tridecanol (800 ml; 4 mole). 168 g (calc. 192) methanol was obtained. 711 g (82%) of product was obtained containing 3.46% Si (calc. 3.23).

A blend of this product (50%) in a DTD 585 mineral oil (50%) had a $-40°$ C. viscosity of 2313 cS. The vapour lock temperature after heating with 0.5% H$_2$O at 100° C. for 72 hours was 225° C.

EXAMPLES 4 to 26

Hydraulic fluids in accordance with the invention were subjected to one or more of the following tests:
(a) Kinematic viscosities at $-40°$ C., in centistokes (CS), were measured in the manner set forth in the SAE J 1703c specification.

(b) Rubber swell properties were evaluated for styrene/butadiene (SBR), nitrile and ethylene/propylene rubbers. In the case of SBR, the test was carried out using standard SAE SBR cups in the manner set forth in the FMVSS 116 DOT 3/4 specification. Rubber swell properties with respect to nitrile rubber were determined by measuring the increase in volume of a 2.54 cm square, 2 mm thick nitrile rubber specimen in 50 mls of test fluid at 120° C. for 70 hours. The test with respect to ethylene/propylene rubber was carried out in the same manner as for nitrile rubber but using ethylene/propylene rubber ring seals (as used in the aviation industry).

(c) Vapour lock temperatures were determined after prior subjection of the fluids to a Humidity Test substantially as described in the FMVSS 116 specification, but without a reference fluid. In the case of fluids comprising a glycol ether base stock, the vapour lock temperatures were determined by the Markey Vapour Lock Test carried out in the apparatus and in the manner as laid down in the SAE J 1705 specification for silicone brake fluids. Vapour lock temperatures for nonglycol ether based fluids were determined by the Gilpin Vapour Lock Test as specified in SAE Paper 710 253 entitled "Operating Performance of motor vehicle braking systems as affected by fluid water content", the Gilpin vapour-lock temperature being taken to be the temperature corresponding with the appearance of 3 ml of bubbles.

(d) Hydrolytic stabilities were determined by heating the test fluid + 10% water in a sealed ampoule for 24 hours at 100° C. and thereafter, on cooling, noting any gelling or separation. (Silanes of Formulae II–IV alone or in admixture with glycol ether base stocks normally gel under these conditions.)

Details of the fluids tested and of the results obtained are given in Tables 1–3.

The abbreviations and commercial products referred to in Tables 1–3 are as follows:

| | |
|---|---|
| Butyl Monoglycol | Ethylene glycol mono butyl ether |
| DPM | Dipropylene glycol mono methyl ether |
| MTG | Triethylene glycol mono methyl ether |
| MDG | Diethylene glycol mono methyl ether |
| Mineral Oil A | Naphthenic mineral oil having a viscosity of 130 cS at $-40°$ F., 3.5 cS at 100° F., and 1.31 cS at 210° F., pour point $>-70°$ F., Boiling point 248 C. Flash point 208° C. aniline pt. 76° C. |
| Mineral Oil D | Ditridecyl dodecanedioate |
| Refrigerant Oil B | Commercially available refrigerant oil manufactured by British Petroleum under the trade mark ZERICE S 53 and believed to be a mixture of alkylated benzenes. |
| Refrigerant Oil C | A blend of naphthenic mineral oils:relative density 0.920, Viscosity at 100° F. 63.0 cS, Viscosity at 210° F. 6.1 cS, Open Flash point 183° C., pour point $-36°$ C. |
| Silicone Fluid | Commercially available silicone brake fluid supplied by Dow Corning under the designation |

| | |
|---|---|
| E 555 | 02-1062 Commercially available ethylene/propylene glycol ether supplied by Dow Chemical Company having a molecular weight of about 243 and wherein the terminal ether alkyl groups are believed to be predominantly methyl but with a proportion being ethyl. |
| A 79 Nitrile Rubber | Commercially available nitrile rubber - as used in Girling brake systems. |

TABLE 1

| Example No | Silane Derivative Tested | % Silane Derivative in MTG | Rubber Swell SAE SBR cup 120° C. 70 Hrs. (% Increase) | Viscosity at −40° (cS) | Markey Vapour Lock Temp (° C.) |
|---|---|---|---|---|---|
| 4 | Tris (butylmonoglycol)-3-butyl-monoglycol propyl silane | 15 * | 20.3 | 371.2 | 140.5 (slightly cloudy) |
| 5 | Tris (DPM) (3-DPM propyl) silane | 40 | 13.2 | 502.7 | 141 |
| 6 | Bis (MTG) (3-MTG propyl) methyl silane | 30 | 6.8 | 621 | 152.5 |
| 7 | MTG-dimethyl-(MTG methyl) silane | 20 | 10.9 | 252.7 | 147 |
| 8 | Tris (MTG) (3-MTG propyl) silane | 80 | 4.2 | 1360 | 187 |
| 9 | Tris (MTG (3-MTG propyl) silane | 50 | 5.8 | 718 | 158 |
| 10 | Tris (MTG) (3-MTG propyl) silane | 5 | 12.4 | | 150 |
| 11 | Tris (MDG) (3-MDG propyl) silane | 100 | 13.6 | 790 | 208.5 |
| 12 | Tris (MDG) (3-MDG propyl) silane | 60 | 8.2 | 462 | 179 |

* In ETG. (Compound not soluble in MTG)

TABLE 2

| Example No. | Silane Derivative Tested | Base Oil | Silane Derivative % in Base Oil | Rubber Swell A79 Nitrile Rubber 120° C. 70 Hrs (% Increase) | Viscosity at −40° (cS) | Gilpin Vapour Lock Temp (° C) |
|---|---|---|---|---|---|---|
| 13 | Tris (butylmonoglycol)-3-butyl monoglycolpropyl silane | Mineral Oil A | 20 | 16.0 | 130 | 190 |
| 14 | Tris (butyl monoglycol)-3-butyl monoglycolpropyl silane | Refrigerant Oil B | 1 | −2.0 | | 280 |
| 15 | Tris (DPM) (3DPM propyl) silane | Tributyl Phosphate | 20 | 15.25* | 519.5 | 126 |
| 16 | Tris (tridecaroxy) (3-tridecanoxypropyl) silane | Mineral Oil A | 20 | 11.14 | 343 | 226 |
| 17 | Tris (tridecanoxy) (3-tridecanoxypropyl) silane | Mineral Oil A | 60 | 12.4 | 3930 | 213 |
| 18 | Tris (DPM) (3-DPM-2-methylpropyl) silane | Refrigerant Oil C | 1 | 8.8 | | 280 |
| 19 | Tris (DPM) (3-DPM-2-methylpropyl) silane | Mineral Oil D | 15 | 3.7 | | |
| 20 | Tris (DPM) (3-DPM-2-methylpropyl silane | Mineral Oil A | 15 | 12.1 | | 215 |
| 21 | Tris (2-ethylhexanoxy)-3-(2-ethylhexanoxy) propyl silane | Silicone Fluid | 20 | | 324 | 232 |

*Test carried out using Ethylene/Propylene Rubber ring seals (as used in the aviation industry).

TABLE 3

| Ex. No | Test Fluid | Hydrolytic Stability |
|---|---|---|
| 22 | Bis (E555)-dimethyl silane - 10% Tris (MDG) (3-MDG propyl)silane - 90% | Clear, mobile, no sediment |
| 23 | Tris (DPM)-methyl silane - 40% Tris (DPM) (3-DPM propyl)silane - 60% | Mobile - not star bright, some deposit believed due to impurity of products, otherwise satisfactory |
| 24 | Tris (DPM)-methyl silane - 10% Tris (2-ethylhexanoxy)-3-(2-ethylhexanoxy) propy-silane - 90% | No separation, slightly cloudy, no gelling |
| 25 | Bis (E555)-dimethyl silane - 25% Tris (MDG) (3-MDG propyl)silane - 15% Triethyleneglycolmonoethylether - 60% | Satisfactory |
| 26 | Bis (E555)-dimethyl silane - 20% Tris (MDG) (3-MDG propyl)silane - 20% Triethylene glycol monoethyl ether - 60% | Satisfactory |

We claim:

1. A silane derivative having the general formula:

wherein:
(a) R is a group of the formula $R^4-(OR^5)_m-OR^6-$;
(b) each of $R^1$ and $R^2$ is independently alkyl, alkenyl, aryl, alkaryl or aralkyl, a group of the formula $-OR^3$ or a group of the formula $R^4-(OR^5)_m-OR^6-$;
(c) $R^3$ is a group of the formula $R^4-(OR^5)_m-$ or a group of the formula:

$$R^8-\underset{\underset{OR^9}{|}}{\overset{\overset{R^7}{|}}{Si}}-(OR^5)_m-$$

and each $R^3$ may be the same as or different from any other group $R^3$;
- (d) $R^4$ is alkyl, alkenyl, aryl, alkaryl or aralkyl and each $R^4$ may be the same as or different from any other group $R^4$;
- (e) $R^5$ is an alkylene group and each $R^5$ may be the same as or different from any other group $R^5$;
- (f) $R^6$ is an alkylene group and each $R^6$ may be the same as or different from any other group $R^6$;
- (g) m is an integer and each m may be the same as or different from any other m;
- (h) each of $R^7$ and $R^8$ is independently alkyl, alkenyl, aryl, alkaryl or aralkyl, a group of the formula $-OR^9$ or a group of the formula $R^4-(OR^5-)_m-OR^6-$; and
- (i) $R^9$ is a group of the formula $R^4-(OR^5)_m-$ and each $R^9$ may be the same as or different from any other group $R^9$.

2. A compound as claimed in claim 1 wherein:
- (a) R is a group of the formula $R^4-(OR^5)_m-OR^6-$;
- (b) each of $R^1$ and $R^2$ is independently alkyl containing from 1 to 18 carbon atoms, alkenyl containing from 1 to 18 carbon atoms, phenyl, alkyl substituted phenyl in which the alkyl substituent contains from 1 to 12 carbon atoms or benzyl, a group of the formula $-OR^3$ or a group of the formula $R^4-(OR^5-)_m-OR^6-$;
- (c) $R^3$ is a group of the formula $R^4-(OR^5)_m-$ or a group of the formula:

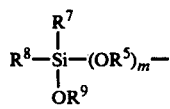

and each $R^3$ may be the same as or different from any other group $R^3$;
- (d) $R^4$ is alkyl containing from 1 to 18 carbon atoms, alkenyl containing from 1 to 18 carbon atoms, phenyl, alkyl substituted phenyl in which the alkyl substituent contains from 1 to 12 carbon atoms or benzyl and each $R^4$ may be the same as or different from any other group $R^4$;
- (e) $R^5$ is an alkylene group containing from 1 to 15 carbon atoms and each $R^5$ may be the same as or different from any other group $R^5$;
- (f) $R^6$ is an alkylene group containing from 1 to 15 carbon atoms and each $R^6$ may be the same as or different from any other group $R^6$;
- (g) m is an integer of from 1 to 4 and each m may be the same as or different from any other m;
- (h) each of $R^7$ and $R^8$ is independently alkyl containing from 1 to 18 carbon atoms, alkenyl containing from 1 to 18 carbon atoms, phenyl, alkyl substituted phenyl in which the alkyl substituent contains from 1 to 12 carbon atoms or benzyl, a group of the formula $-OR^9$ or a group of the formula $R^4-(OR^5)_m-OR^6-$; and
- (i) $R^9$ is a group of the formula $R^4-(OR^5)_m-$ and each $R^9$ may be the same as or different from any other group $R^9$.

3. A compound as claimed in claim 2 wherein each of $R^1$ and $R^2$ is methyl.

4. A compound as claimed in claim 2 wherein $R^5$ is alkylene containing from 1 to 4 carbon atoms.

5. A compound as claimed in claim 4 wherein $R^5$ is ethylene or propylene.

6. A compound as claimed in claim 4 wherein $R^6$ is alkylene containing from 1 to 6 carbon atoms.

7. A compound as claimed in claim 2 wherein each of $R^7$ and $R^8$ is methyl.

8. A compound as claimed in claim 2 which contains a maximum of 2 silicon atoms.

9. Tris(triethyleneglycolmonomethylether)-3-triethyleneglycolmonomethyletherpropyl silane as claimed in claim 1.

10. Tris(diethyleneglycolmonomethylether)-3-diethyleneglycolmonomethyletherpropyl silane as claimed in claim 1.

11. Tris(tridecanoxy)-3-tridecanoxypropyl silane.

12. Tris(ethyleneglycolmonobutylether)-3-ethyleneglycolmonobutyletherpropyl silane as claimed in claim 1.

13. Tris(dipropyleneglycolmonomethylether)-3-dipropyleneglycolmonomethyletherpropyl silane as claimed in claim 1.

14. Bis(triethyleneglycolmonomethylether)-3-triethyleneglycolmonomethyletherpropyl-methyl silane as claimed in claim 1.

15. Triethyleneglycolmonomethylether-dimethyltriethyleneglycolmonomethylethermethyl silane as claimed in claim 1.

16. Tris(2-ethylhexanoxy)-3-(2-ethylhexanoxy)propyl silane.

17. Tris(dipropyleneglycolmonomethylether)-3-dipropyleneglycolmonomethylether-2-methylpropyl silane as claimed in claim 1.

18. A hydraulic fluid comprising at least one compound of Formula I as claimed in claim 1.

19. A hydraulic fluid as claimed in claim 18 comprising from 0.5 to 99% by weight of the compound, based on the total weight of the hydraulic fluid.

20. A hydraulic fluid as claimed in claim 18 comprising at least one conventional hydraulic fluid additive and/or base stock.

21. A hydraulic fluid as claimed in claim 18 consisting essentially of a combination of from 5 to 30% by weight of at least one compound of Formula I and from 5 to 30% by weight of at least one compound having the general formula:

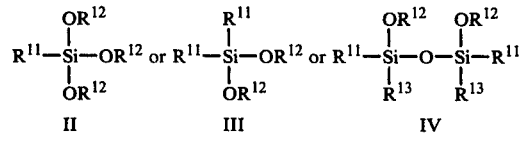

wherein $R^{11}$ is an alkyl or aryl group, $R^{12}$ is an alkyl, aryl, alkaryl or aralkyl group or a group of the formula $R^4-(OR^5)_m-$, $R^{13}$ is an alkyl, aryl, alkaryl or aralkyl group or a group of the formula $R^4-(OR^5)_m-O-$, $R^4$ is alkyl, alkenyl, aryl, alkaryl or aralkyl, $R^5$ is alkylene and m is zero or an integer, in a glycol ether base stock.

22. A hydraulic fluid as claimed in claim 18 consisting essentially of from 10to 90% by weight of at least one compound of Formula I and from 90to 10% by weight of at least one compound having the general formula:

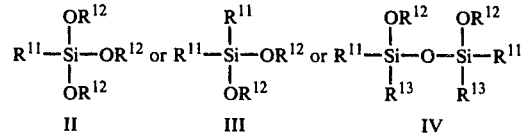

wherein $R^{11}$ is an alkyl or aryl group, $R^{12}$ is an alkyl, aryl, alkaryl or aralkyl group or a group of the formula $R^4\!-\!(OR^5)_m\!-\!$, $R^{13}$ is an alkyl, aryl, alkaryl or aralkyl group or a group of the formula $R^4\!-\!(OR^5)_m\!-\!O\!-\!$, $R^4$ is alkyl, alkenyl, aryl, alkaryl or aralkyl, $R^5$ is alkylene and m is zero or an integer.

23. A hydraulic fluid comprising at least one conventional hydraulic fluid additive and/or base stock and a silane derivative having the general formula:

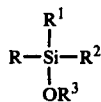  I wherein:
(a) R is a group of the formula $R^4\!-\!(OR^5)_m\!-\!OR^6\!-\!$;
(b) each of $R^1$ and $R^2$ is independently alkyl, alkenyl, aryl, alkaryl or aralkyl, a group of the formula $-OR^3$ or a group of the formula $R^4\!-\!(OR^5)_m\!-\!OR^6\!-\!$;
(c) $R^3$ is a group of the formula $R^4\!-\!(OR^5)_m\!-\!$ or a group of the formula:

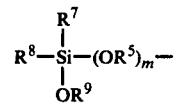

and each $R^3$ may be the same as or different from any other group $R^3$;
(d) $R^4$ is alkyl, alkenyl, aryl, alkaryl or aralkyl and each $R^4$ may be the same as or different from any other group $R^4$;
(e) $R^5$ is an alkylene group and each $R^5$ may be the same as or different from any other group $R^5$;
(f) $R^6$ is an alkylene group and each $R^6$ may be the same as or different from any other group $R^6$;
(g) m is zero or an integer and each m may be the same as or different from any other m;
(h) each of $R^7$ and $R^8$ is independently alkyl, alkenyl, aryl, alkaryl or aralkyl, a group of the formula $-OR^9$ or a group of the formula $R^4\!-\!(OR^5)_m\!-\!OR^6\!-\!$; and
(i) $R^9$ is a group of the formula $R^4\!-\!(OR^5)_m\!-\!$ and each $R^9$ may be the same as or different from any other group $R^9$.

* * * * *